United States Patent
Magee et al.

(10) Patent No.: US 9,610,303 B2
(45) Date of Patent: Apr. 4, 2017

(54) GLUCAN PREPARATIONS

(75) Inventors: Andrew Magee, Maynard, MA (US); James Rolke, Woburn, MA (US); Ren-der Yang, Shrewsburg, MA (US)

(73) Assignee: BIOTHERA, INC., Minneapolis, MN (US)

( * ) Notice: Subject to any disclaimer, the term of this patent is extended or adjusted under 35 U.S.C. 154(b) by 677 days.

(21) Appl. No.: 11/818,741

(22) Filed: Jun. 15, 2007

(65) Prior Publication Data

US 2008/0103112 A1    May 1, 2008

Related U.S. Application Data

(60) Provisional application No. 60/813,971, filed on Jun. 15, 2006.

(51) Int. Cl.
*A61K 31/716* (2006.01)
*C08B 37/00* (2006.01)
*C08L 5/00* (2006.01)

(52) U.S. Cl.
CPC ........ *A61K 31/716* (2013.01); *C08B 37/0024* (2013.01); *C08L 5/00* (2013.01)

(58) Field of Classification Search
CPC ...... A61K 31/716; C08L 5/00; C08G 37/0024
See application file for complete search history.

(56) References Cited

U.S. PATENT DOCUMENTS

| | | |
|---|---|---|
| 4,810,646 A | 3/1989 | Jamas et al. |
| 4,962,094 A | 10/1990 | Jamas |
| 5,028,703 A | 7/1991 | Jamas et al. |
| 5,032,401 A | 7/1991 | Jamas |
| 5,082,936 A | 1/1992 | Jamas |
| 5,250,436 A | 10/1993 | Jamas |
| 5,322,841 A | 6/1994 | Jamas |
| 5,397,773 A | 3/1995 | Donzis |
| 5,488,040 A | 1/1996 | Jamas |
| 5,504,079 A | 4/1996 | Jamas |
| 5,506,124 A | 4/1996 | Jamas |
| 5,519,009 A | 5/1996 | Donzis |
| 5,532,223 A | 7/1996 | Jamas |
| 5,576,015 A | 11/1996 | Donzis |
| 5,607,677 A | 3/1997 | Jamas |
| 5,622,939 A | 4/1997 | Jamas |
| 5,622,940 A | 4/1997 | Ostroff |
| 5,633,369 A | 5/1997 | Jamas |
| 5,663,324 A | 9/1997 | Jamas |
| 5,702,719 A | 12/1997 | Donzis |
| 5,705,184 A | 1/1998 | Donzis |
| 5,741,495 A | 4/1998 | Jamas |
| 5,783,569 A | 7/1998 | Jamas |
| 5,811,542 A | 9/1998 | Jamas |
| 5,817,643 A | 10/1998 | Jamas |
| 5,849,720 A | 12/1998 | Jamas |
| 6,020,324 A | 2/2000 | Jamas |
| 6,046,323 A | 4/2000 | Park |
| 6,084,092 A | 7/2000 | Wakshull |
| 6,090,938 A | 7/2000 | Wakshull |
| 6,110,692 A | 8/2000 | Wakshull |
| 6,117,850 A | 9/2000 | Patchen |
| 6,143,731 A | 11/2000 | Jamas |
| 6,143,883 A | 11/2000 | Lehmann et al. |
| 6,214,337 B1 | 4/2001 | Hayen et al. |
| 6,242,594 B1 | 6/2001 | Kelly et al. |
| 6,294,321 B1 | 9/2001 | Wakshull |
| 6,369,216 B1 | 4/2002 | Patchen |
| 6,413,715 B2 | 7/2002 | Wakshull |
| 6,630,310 B1 | 10/2003 | Wakshull |
| 7,022,685 B2 | 4/2006 | Patchen |
| 2002/0032170 A1 | 3/2002 | Jamas et al. |
| 2004/0014715 A1 | 1/2004 | Ostroff |
| 2004/0082539 A1 | 4/2004 | Kelly |
| 2004/0116380 A1 | 6/2004 | Jamas et al. |
| 2005/0245480 A1 | 11/2005 | Ostroff |
| 2006/0009419 A1 | 1/2006 | Ross |
| 2006/0165700 A1 | 7/2006 | Ostroff |
| 2006/0247205 A1 | 11/2006 | Patchen |
| 2007/0042930 A1 | 2/2007 | Ross |
| 2007/0059310 A1 | 3/2007 | Karel |
| 2008/0063650 A1 | 3/2008 | Yan |
| 2008/0108114 A1 | 5/2008 | Cox |
| 2008/0167268 A1 | 7/2008 | Yan |

FOREIGN PATENT DOCUMENTS

| | | |
|---|---|---|
| CN | 101553261 A | 10/2009 |
| EP | 2032180 A2 | 3/2009 |
| HK | 1138215 A | 10/2014 |
| JP | 5503952 A | 6/1993 |
| JP | 6107702 A | 4/1994 |
| JP | 2001-342257 | 12/2001 |
| JP | 2002-105101 | 4/2002 |
| JP | 2006507239 A | 3/2006 |
| JP | 2008500623 A | 1/2008 |
| JP | 2009-515512 | 4/2009 |
| JP | 2011501691 A | 1/2011 |
| JP | 2014-025079 A | 2/2014 |
| JP | 2009540106 A | 11/2015 |
| SG | 164426 A | 9/2010 |
| WO | 9103495 A1 | 3/1991 |
| WO | 9404163 A1 | 3/1994 |
| WO | 2004/014320 A2 | 2/2004 |
| WO | WO-2004033502 A1 | 4/2004 |
| WO | WO-2005120251 A1 | 12/2005 |
| WO | 2007146416 A3 | 12/2007 |

OTHER PUBLICATIONS

Daou, C., Zhang, H. (2012) Oat Beta-Glucan: Its Role in Health Promotion and Prevention of Diseases. Comprehensive Reviews in Food Science and Food Safety, vol. 11, p. 355-365.*

Hunter, et al., "Preparation of microparticulate beta-glucan from *Saccharomyces cerevisiae* for use in immune potentiation", *Letters in Applied Microbiology*, 35, (2002), pp. 267-271.

"PCT International Search Report and Written Opinion of the International Searching Authority", PCT/US2007/14055, (Nov. 30, 2007), 6 pages.

(Continued)

*Primary Examiner* — Leigh C Maier
(74) *Attorney, Agent, or Firm* — Wilson, Sonsini, Goodrich & Rosati

(57) ABSTRACT

Particulate β-glucan is solubilized at elevated pressure and temperature to form soluble β-glucan. The method is safe and economical and produces a product that is an improved pharmaceutical agent.

19 Claims, 2 Drawing Sheets

(56) References Cited

OTHER PUBLICATIONS

Bacon, et al., "The Glucan Components of the Cell Wall of Baker's Yeast (*Saccharomyces cerevisiae*) Considered in Relation to its Ultrastructure", *Biochem. J.*, vol. 114, (1969), pp. 557-567.

Bell, et al., "The Structure of a Cell-wall Polysaccharide of Baker's Yeast", (1950), pp. 1944-1947.

Hassid, et al., "The Molecular Constitution of an Insoluble Polysaccharide from Yeast, *Saccharomyces cerevisiae*", *Contribution from the Divisions of Plant Nutrition and Fruit Products, College of Agriculture*, University of California,(Jan. 1941), pp. 295-298.

Manners, et al., "The Structure of a beta-(1-->3)-D-Glucan from Yeast Cell Walls", *Biochem. J.*, vol. 135, (1973), pp. 19-30.

Misaki, et al., "Structure of the Cell-Wall Glucan of Yeast (*Saccharomyces cerevisiae*)", *Carbohydrate Research*, vol. 6, (1968), pp. 150-164.

U.S. Appl. No. 12/151,666 entitled "Soluble Glucan Preparation", filed May 8, 2008.

U.S. Appl. No. 60/975,734 entitled "The Use of Beta-Glucan on Upper Respiratory Tract Infection Symptoms and Psychological Well-Being", filed Sep. 27, 2007.

U.S. Appl. No. 12/150,049 entitled "Therapeutic Beta-Glucan Combinations", filed Apr. 4, 2008.

U.S. Appl. No. 11/818,697 entitled "Glucan Compositions and Methods of Enhancing CR3 Dependent Neutrophil-Mediated Cytotoxicity", filed Jun. 15, 2007.

U.S. Appl. No. 11/579,467 entitled "Whole Glucan Particles in Combination With Antibodies,Vaccines and Viral Monoclonal Antibodies", filed May 10, 2005.

Blagovic et al. Lipid composition of brewer's yeast. Food Technol. Biotechnol. 39:175-181 (2001).

Deman. Chapter 2. Lipids in Principles of Food Chemistry @ 1985. AVI Publishing Co., Inc.

Nawar. Chapter 4. Lipids in Food Chemistry. © 1985. Editor: Owen R. Fennema. Marcel Dekker, Inc.

PCT/US2007/014055 International Preliminary Report on Patentability dated Dec. 16, 2008.

Van Der Rest et al. The plasma membrane of *Saccharomyces cerevisiae*: structure, function, and biogenesis. Microbiol Rev. 59(2):304-322 (1995).

\* cited by examiner

GLUCAN PREPARATIONS

This application claims the benefit of U.S. Ser. No. 60/813,971 entitled GLUCAN PREPARATIONS, filed on Jun. 15, 2006.

BACKGROUND OF THE INVENTION

The present invention relates to compositions that include β-glucan. More particularly, the present invention relates to soluble β-glucan compositions and their use in stem cell mobilization.

Glucans are generally described as polymers of glucose and are derived from yeast, bacteria, fungi and plants such as oats and barley. Glucans containing a β(1-3)-linked glucopyranose backbone are known to have biological activity, specifically they have been shown to modulate the immune system and more recently to induce hematopoietic stem and progenitor cell (HSPC) mobilization.

Treatment of various cancers increasingly involves cytoreductive therapy, including high dose chemotherapy or radiation. These therapies decrease a patient's white blood cell counts, suppress bone marrow hematopoietic activity, and increase their risk of infection and/or hemorrhage. As a result, patients who undergo cytoreductive therapy must also receive therapy to reconstitute bone marrow function (hematopoiesis).

Despite advances in stem cell mobilization and techniques, up to 20-25% of patients exhibit poor mobilization and are not able to proceed with auto-transplantation. PGG β-glucan is a soluble yeast-derived polysaccharide and has been shown previously to induce hematopoietic stem and progenitor cell (HSPC) mobilization.

SUMMARY OF THE INVENTION

In the present invention, yeast is cultured, harvested and purified to yield particulate β-glucan essentially free of contaminating volatile organic compounds (VOCs). Particulate β-glucan is prepared by subjecting yeast cells or fragments thereof to a series of alkaline, surfactant, and acidic extractions that remove host cell impurities.

Particulate β-glucan, produced by the above process or by prior art methods, is solubilized in an acidic solution at elevated temperature and pressure. The resulting soluble β-glucan is then clarified and purified using hydrophobic interaction chromatography (HIC) followed by gel-permeation chromatography (GPC). As a pharmaceutical agent, the soluble β-glucan can be administered at higher doses without increasing, or in fact decreasing, observed side effects or adverse events.

DETAILED DESCRIPTION OF THE INVENTION

Particulate β-Glucan

Figure 1:
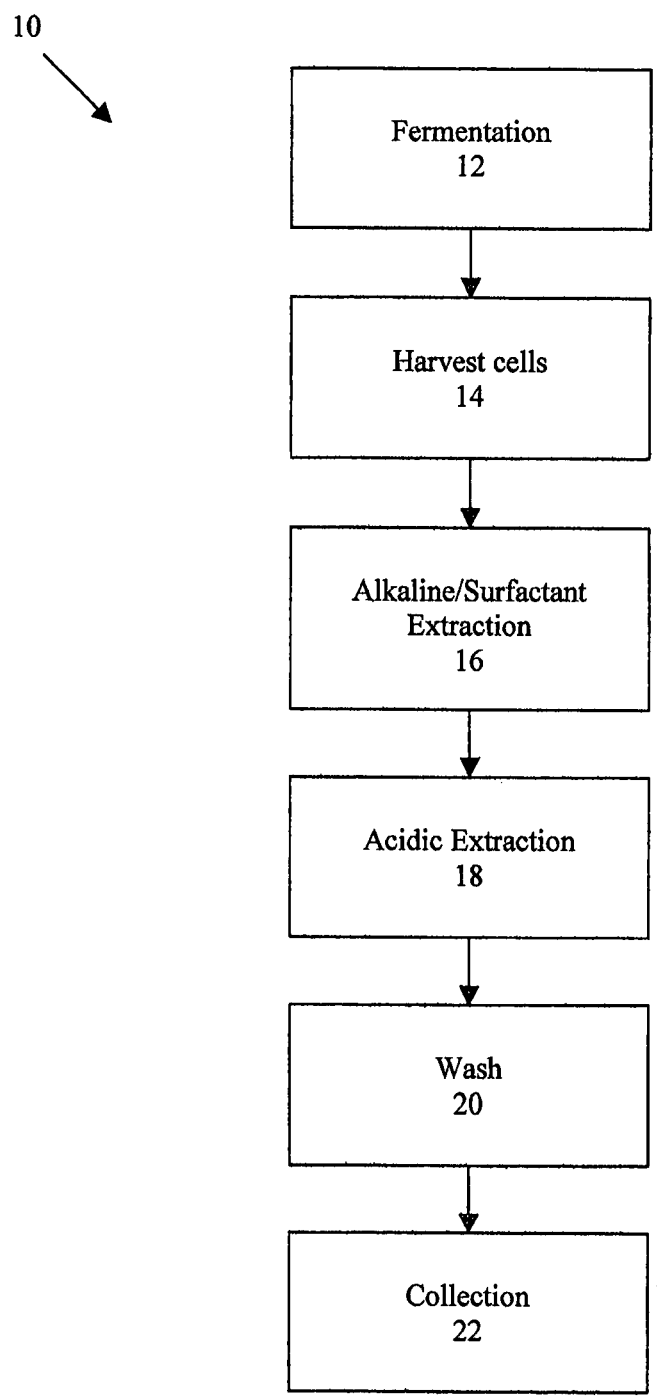
FIG. 1 is a schematic representation of a process for producing particulate β-glucan.

FIG. 1 is an overview of method 10, which includes steps 12-22, for producing insoluble, or particulate, β-glucan from yeast. In step 12, a yeast culture is grown, typically, in a shake flask or fermenter. The yeast strain utilized for the present invention can be any strain, examples of which include Saccharomyces (S.) cerevisiae, S. delbrueckii, S. rosei, S. microellipsodes, S. carlsbergensis, S. bisporus, S. fermentati, S. rouxii, Schizosaccharomyces pombe, Kluyveromyces (K.) lactis, K. fragilis, K. polysporus, Candida (C.) albicans, C. cloacae, C. tropicalis, C. utilis, Hansenula (H.) wingei, H. arni, H. henricii, H. americana, H. canadiensis, H. capsulata, H. polymorpha, Pichia (P.) kluyveri, P. pastoris, P. polymorpha, P. rhodanesis, P. ohmeri, Torulopsis (T.) bovina and T. glabrata.

In one embodiment of bulk production, a culture of yeast is started and expanded stepwise through a shake flask culture into a 250-L scale production fermenter. The yeast are grown in a glucose-ammonium sulfate medium enriched with vitamins, such as folic acid, inositol, nicotinic acid, pantothenic acid (calcium and sodium salt), pyridoxine HCl and thymine HCl and trace metals from compounds such as ferric chloride, hexahydrate; zinc chloride; calcium chloride, dihydrate; molybdic acid; cupric sulfate, pentahydrate and boric acid. An antifoaming agent such as Antifoam 204 may also be added at a concentration of about 0.02%.

The production culture is maintained under glucose limitation in a fed batch mode. During seed fermentation, samples are taken periodically to measure the optical density of the culture before inoculating the production fermenter. During production fermentation, samples are also taken periodically to measure the optical density of the culture. At the end of fermentation, samples are taken to measure the optical density, the dry weight, and the microbial purity.

If desired, fermentation may be terminated by raising the pH of the culture to at least 11.5 or by centrifuging the culture to separate the cells from the growth medium. In addition, depending on the size and form of purified β-glucan that is desired, steps to disrupt or fragment the yeast cells may be carried out. Any known chemical, enzymatic or mechanical methods, or any combination thereof may be used to carry out disruption or fragmentation of the yeast cells.

At step 14, the yeast cells containing the β-glucan are harvested. When producing bulk β-glucan, yeast cells are typically harvested using continuous-flow centrifugation.

Step 16 represents the initial extraction of the yeast cells utilizing one or more of an alkaline solution, a surfactant, or a combination thereof. A suitable alkaline solution is, for example, 0.1 M-5 M NaOH. Suitable surfactants include, for example, octylthioglucoside, Lubrol PX, Triton X-100, sodium lauryl sulfate (SDS), Nonidet p-40, Tween 20 and the like. Ionic (anionic, cationic, amphoteric) surfactants (e.g., alkyl sulfonates, benzalkonium chlorides, and the like) and nonionic surfactants (e.g., polyoxyethylene hydrogenated castor oils, polyoxyethylene sorbitol fatty acid esters, polyoxyethylene sorbitan fatty acid esters, polyoxyethylene glycerol fatty acid esters, polyethylene glycol fatty acid esters, polyoxyethylene alkyl phenyl ethers, and the like) may also be used. The concentration of surfactant will vary and depend, in part, on which surfactant is used. Yeast cell material may be extracted one or more times.

Extractions are usually carried out at temperatures between about 70° C. and about 90° C. Depending on the temperature, the reagents used and their concentrations, the duration of each extraction is between about 30 minutes and about 3 hours.

After each extraction, the solid phase containing the β-glucan is collected using centrifugation or continuous-flow centrifugation and resuspended for the subsequent step. The solubilized contaminants are removed in the liquid phase during the centrifugations, while the β-glucan remains in the insoluble cell wall material.

In one embodiment, four extractions are carried out. In the first extraction, harvested yeast cells are mixed with 1.0 M NaOH and heated to 90° C. for approximately 60 minutes. The second extraction is an alkaline/surfactant extraction whereby the insoluble material is resuspended in 0.1 M NaOH and about 0.5% to 0.6% Triton X-100 and heated to 90° C. for approximately 120 minutes. The third extraction is similar to the second extraction except that the concentration of Triton X-100 is about 0.05%, and the duration is shortened to about 60 minutes. In the fourth extraction, the insoluble material is resuspended in about 0.5% Triton-X 100 and heated to 75° C. for approximately 60 minutes.

The alkaline and/or surfactant extractions solubilize and remove some of the extraneous yeast cell materials. The alkaline solution hydrolyzes proteins, nucleic acids, mannans, and lipids. Surfactant enhances the removal of lipids and other hydrophobic impurities, which provides an additional advantage yielding an improved β-glucan product.

Previous purification procedures resulted in β-glucan containing minute amounts of volatile organic compounds (VOCs). Previous studies have shown that VOCs are produced by the release of fat as free fatty acid, which quickly decomposes into various VOCs. In most cases, the amounts detected are not enough to cause harm, however, it is an obvious benefit to have a product that is administered to humans or other animals that is essentially free of any VOCs.

Fat content of the yeast *Saccharomyces cerevisiae* produced by aerobic and anaerobic growth ranges from about 3% to about 8%. The fat content varies depending on growth conditions of the yeast. Table 1 provides an overview of the typical fat composition of the yeast *Saccharomyces cerevisiae*. The data is from the following references:

Blagovic, B., J. Rpcuc, M. Meraric, K. Georgia and V. Maric. 2001. Lipid composition of brewer's yeast. Food Technol. Biotechnol. 39:175-181.

Shulze. 1995. Anaerobic physiology of *Saccharomyces cerevisiae*. Ph.D. Thesis, Technical University of Denmark.

Van Der Rest, M. E., A. H. Kamming, A Nakano, Y. Anrak, B. Poolman and W. N. Koning. 1995. The plasma membrane of *Saccharomyces cerevisiae*: structure, function and biogenesis. Microbiol. Rev. 59:304-322.

TABLE 1

| Fatty acid | Shulze (1995) | Blagovic et al (2001) (anaerobic growth) | Van Der Rest et al (1995) |
|---|---|---|---|
| 10:0 Capric acid | 1.1% | | |
| 12:0 and 12:1 Lauric acid | 4.8% | 7.3% | |
| 14:0 and 14:1 Myristic acid | 8.8% | 5.1% | 7.0*% |
| 16:0 Palmitic acid | 26.8% | 44.2% | 12.8% |
| 16:1 Palmitoleic acid | 16.6% | 16.9% | 32.3% |
| 18:0 Stearic acid | 6.1% | 13.9% | 8.0% |
| 18.1 Oleic acid | 25.7% | 7.3% | 28.0% |
| 18:2 and higher Linoleic acid, arachadonic acid and others | 10.1% | 5.3% | 9.4% |

*includes lipids 10:0 to 14:1

Yeast cell wall material typically contains 10-25% fat depending on yeast type and growth conditions. Presently, during processing of yeast cell wall material into β-glucan, some, but not all fat is removed by centrifugation and wash steps. Thus, a typical preparation might yield a fat content of 3-7%.

The manufacturing process typically involves steps to remove mannoproteins, lipids and other undesirable components of the yeast cell wall. Some key steps common to this processing are various wash steps that employ acid and alkali in separate washing steps to liberate certain cell wall components. Several of the steps use an alkali wash process where an alkali, usually sodium hydroxide, is added to the liquid cell wall suspension. One of the purposes of the alkali is to remove lipid by forming the free fatty acids of the lipid. The result is a reduction in fat content of the β-glucan.

The alkali wash steps commonly used in production of yeast β-glucan leave behind residual fatty acids and partially degraded fat triglycerides that have increased reactivity. The direct result of the alkali wash process is the release of reactive free fatty acids that quickly decompose to various oxidative products of fat decomposition.

Numerous researchers have detailed the fact that polyunsaturated fats decompose during storage. Although a triglyceride can autoxidize in the presence of oxygen, it is more common for free fatty acids to undergo oxidative decomposition. The normal step in the decomposition of a lipid, also known as a triglyceride, is the liberation of the free fatty acid from the triglyceride. Free fatty acids are virtually nonexistent in the tissues of living organisms, but decomposition is common when the organism dies or is harvested for further processing such as occurs with oilseeds and in rendering of animal fat. (Nawar, W. W. Chapter 4. Lipids. In: Food Chemistry.© 1985. Editor: Owen R. Fennema. Marcel Dekker, Inc.; DeMan, J. M. Chapter 2. Lipids In: Principles of Food Chemistry© 1985. AVI Publishing Co., Inc.) In many triglycerides, the 2-position of the glyceride molecule is occupied by an unsaturated fat. In the case of alkali treatment of β-glucan it is the well-known process of saponification that is releasing unsaturated fatty acids that decompose as described below.

The process of fat oxidation has several mechanisms. The most common mechanism is autoxidation. The process is initiated by the removal of hydrogen from an olefenic compound to create a free radical. The removal of hydrogen takes place at the carbon atom next to the double bond in the fat. The reaction is initiated by various free-radical generating factors such as UV light, metals, singlet oxygen, etc.

RH→R.+H. (creation of a free radical electron)

The second step is the addition of oxygen to cause formation of a peroxy-free radical, which propagates the chain reaction by extracting hydrogen from another unsaturated fatty acid.

R.+$O_2$→$RO_2$. (formation of reactive oxygenated free radical)

$RO_2$.+RH→ROOH+R. (ROOH is the reactive hydroperoxide that decomposes to secondary reaction products such as VOCs)

The chain reaction continues until it is terminated by free radicals combining with themselves to yield nonreactive products.

R.+R.→R—R

R.+$RO_2$.→$RO_2$R

The following are the chemical reactions that occur to form the VOCs. Linoleic acid is used as a model for the chemistry, but there are other unsaturated fatty acids present in the yeast cell wall and in yeast β-glucan preparations that produce the same end products.

ROOH→RO.+OH—

RO.→cleavage reactions form aldehydes, alkyl radicals (which form hydrocarbons and alcohols), esters, alcohols, and hydrocarbons.

EXAMPLE

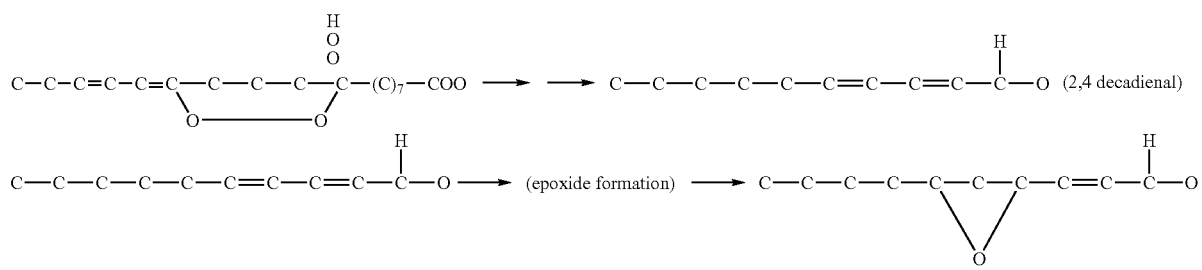

Decomposition of the epoxide produces several products including →C—C—C—C—C—C (hexane)+O═C—C═C—C═O (2-butene-1,4 dial)

Similarly, if the epoxide forms between the 2 and 3 carbon bonds the chemistry leads to:

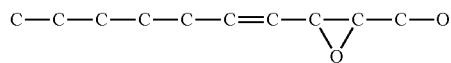

(2,3 epoxide of 2,4-decadienal)→ethanol and 2-octenal

In a similar manner, the formation of any VOCs identified in β-glucan preparations can be accounted for by the autoxidation reactions that occur with decomposition of the reactive species of peroxides formed during fatty acid oxidation. Therefore, the removal of as much fat from β-glucan preparations as possible creates a product that is more pure not only in terms of fat but also in terms of VOC contamination.

Referring back to FIG. 1, the next step in the purification process is an acidic extraction shown at step 18, which removes glycogen. One or more acidic extractions are accomplished by adjusting the pH of the alkaline/surfactant extracted material to between about 5 and 9 and mixing the material in about 0.05 M to about 1.0 M acetic acid at a temperature between about 70° C. and 100° C. for approximately 30 minutes to about 12 hours.

In one embodiment, the insoluble material remaining after centrifugation of the alkaline/surfactant extraction is resuspended in water, and the pH of the solution is adjusted to about 7 with concentrated HCl. The material is mixed with enough glacial acetic acid to make a 0.1 M acetic acid solution, which is heated to 90° C. for approximately 5 hours.

At step 20, the insoluble material is washed. In a typical wash step, the material is mixed in purified water at about room temperature for a minimum of about 20 minutes. The water wash is carried out two times. The purified β-glucan product is then collected, as shown by step 22. Again, collection is typically carried out by centrifugation or continuous-flow centrifugation.

At this point, a purified, particulate β-glucan product is formed. The product may be in the form of whole glucan particles or any portion thereof, depending on the starting material. In addition, larger sized particles may be broke down into smaller particles. The range of product includes β-glucan particles that have substantially retained in vivo morphology (whole glucan particles) down to submicron-size particles.

As is well known in the art, particulate β-glucan is useful in many food, supplement and pharmaceutical applications. Alternatively, particulate β-glucan can be processed further to form aqueous, soluble β-glucan.

Soluble β-Glucan

Figure 2:
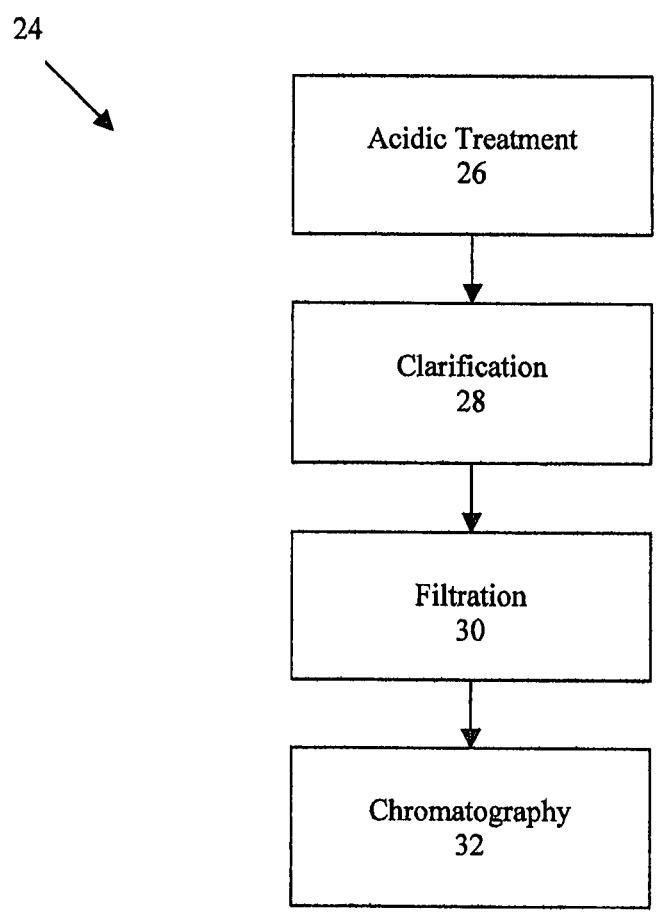
FIG. 2 is a schematic representation of a process for producing soluble β-glucan.

FIG. 2 is an overview of method 24, which includes steps 26-32, for producing aqueous, soluble β-glucan. The starting material used in method 24 is particulate β-glucan, which may be produced by method 10 or produced by any of a number of previously used methods. The particulate β-glucan starting material may range in size from whole glucan particles down to submicron-sized particles.

In step 26, particulate β-glucan undergoes an acidic treatment under pressure and elevated temperature to produce soluble β-glucan. Pelleted, particulate β-glucan is resuspended and mixed in a sealable reaction vessel in a buffer solution and brought to pH 3.6. Buffer reagents are added such that every liter, total volume, of the final suspension mixture contains about 0.61 g sodium acetate, 5.24 ml glacial acetic acid and 430 g pelleted, particulate β-glucan. The vessel is purged with nitrogen to remove oxygen and increase the pressure within the reaction vessel.

In a particular embodiment, the pressure inside the vessel is brought to 35 PSI, and the suspension is heated to about 135° C. for between about 4.5 and 5.5 hours. It was found that under these conditions the β-glucan will solubilize. As the temperature decreases from 135° C., the amount of solubilization also decreases.

It should be noted that this temperature and pressure are required in the embodiment just described. Optimization of temperatures and pressures may be required if any of the reaction conditions and/or reagents are altered.

The increased pressure and temperature imparts advantages over prior art processes for solubilizing β-glucan by virtually eliminating the use of hazardous chemicals from the process. Hazardous chemicals that have previously been used include, for example, flammable VOCs such as ether and ethanol, very strong acids such as formic acid and sulphuric acid and caustic solutions of very high pH. The present process is not only safer, but, by reducing the number of different chemicals used and the number of steps involved, is more economical.

The exact duration of heat treatment is typically determined experimentally by sampling reactor contents and performing gel permeation chromatography (GPC) analyses. The objective is to maximize the yield of soluble material that meets specifications for high resolution-GPC (HR-GPC) profile and impurity levels, which are discussed below. Once the β-glucan is solubilized, the mixture is cooled to stop the reaction.

The crude, solubilized β-glucan may be washed and utilized in some applications at this point, however, for pharmaceutical applications further purification is performed. Any combination of one or more of the following steps may be used to purify the soluble β-glucan. Other means known in the art may also be used if desired. At step 28, the soluble β-glucan is clarified. Suitable clarification means include, for example, centrifugation or continuous-flow centrifugation.

Next, the soluble β-glucan may be filtered as shown by step 30. In one embodiment, the material is filtered, for example, through a depth filter followed by a 0.2 μm filter.

Step 32 utilizes chromatography for further purification. The soluble β-glucan may be conditioned at some point during step 28 or step 30 in preparation for chromatography. For example, if a chromatographic step includes hydrophobic interaction chromatography (HIC), the soluble β-glucan can be conditioned to the appropriate conductivity and pH with a solution of ammonium sulphate and sodium acetate. A suitable solution is 3.0 M ammonium sulfate, 0.1 M sodium acetate, which is used to adjust the pH to 5.5.

In one example of HIC, a column is packed with Tosah Toyopearl Butyl 650M resin (or equivalent). The column is packed and qualified according to the manufacturer's recommendations.

Prior to loading, the column equilibration flow-through is sampled for pH, conductivity and endotoxin analyses. The soluble β-glucan, conditioned in the higher concentration ammonium sulphate solution, is loaded and then washed. The nature of the soluble β-glucan is such that a majority of the product will bind to the HIC column. Low molecular weight products as well as some high molecular weight products are washed through. Soluble β-glucan remaining on the column is eluted with a buffer such as 0.2 M ammonium sulfate, 0.1 M sodium acetate, pH 5.5. Multiple cycles may be necessary to ensure that the hexose load does not exceed the capacity of the resin. Fractions are collected and analyzed for the soluble β-glucan product.

Another chromatographic step that may be utilized is gel permeation chromatography (GPC). In one example of GPC, a Tosah Toyopearl HW55F resin, or equivalent is utilized and packed and qualified as recommended by the manufacturer. The column is equilibrated and eluted using citrate-buffered saline (0.14 M sodium chloride, 0.011 M sodium citrate, pH 6.3). Prior to loading, column wash samples are taken for pH, conductivity and endotoxin analyses. Again, multiple chromatography cycles may be needed to ensure that the load does not exceed the capacity of the column.

The eluate is collected in fractions, and various combinations of samples from the fractions are analyzed to determine the combination with the optimum profile. For example, sample combinations may be analyzed by HR-GPC to yield the combination having an optimized HR-GPC profile. In one optimized profile, the amount of high molecular weight (HMW) impurity, that is soluble β-glucans over 380,000 Da, is less than or equal to 10%. The amount of low molecular weight (LMW) impurity, under 25,000 Da, is less than or equal to 17%. The selected combination of fractions is subsequently pooled.

At this point, the soluble β-glucan is purified and ready for use. Further filtration may be performed in order to sterilize the product. If desired, the hexose concentration of the product can be adjusted to about 1.0±0.15 mg/ml with sterile citrate-buffered saline.

The purification techniques described above result in an improved soluble β-glucan that provides specific advantages as a pharmaceutical agent, which are discussed below. The soluble β-glucan has an average molecular weight between about 120,000 Da and about 205,000 Da and a molecular weight distribution (polydispersity) of not more than 2.5 as determined by HR-GPC with multiple angle light scattering (HR-GPC/MALS) and differential refractive index detection. Powder X-ray diffraction and magic-angle spinning NMR determined that the product consists of polymeric chains associated into triple helices.

The soluble β-glucan is typically uncharged and therefore has no $pK_a$. It is soluble in water independent of pH, and the viscosity increases as the concentration increases.

Table 2 summarizes the typical levels of impurities in a soluble β-glucan product utilizing whole glucan particles produced by method 10.

TABLE 2

| Impurity | Specification | Range of Levels Observed in 3 Batches |
|---|---|---|
| HMW (>380 kD) | ≤10% | 4-8% |
| LMW (<25 kD) | ≤17% | 8-13% |
| Reducing sugar | 0.7-1.6% of total hexose* | 1.0-1.1% of total hexose |
| Glycogen | ≤10% of total hexose | <5% of total hexose |
| Mannan (as mannose) | ≤1% of recovered hexose | <0.6 to ≤0.8% of recovered hexose |
| Chitin (as glucosamine) | ≤2% of total hexose | 0.2-0.5% of total hexose |
| Protein | ≤0.2% of total hexose | <0.2% of total hexose |
| Yeast protein | Characterization** | <2 ng/mg hexose |
| DNA | Characterization | <6.5 to <50 pg/mg hexose |
| Ergosterol | Characterization | <10 to <25 μg/mg hexose |
| Triton X-100 | Characterization | <1 to <5 μg/mg hexose |
| Antifoam 204 | Characterization | <10 μg/mg hexose |

*Total hexose is determined by a colorimetric assay. Sugar polymers are hydrolyzed in sulphuric acid and anthrone to form furfurals. The furfurals conjugate with the anthrone to yield a chromophore, which is measured spectrophotometrically.
**Limits were not specified.

Product-related impurities include material with molecular weights greater than 380,000 daltons or less than 25,000 daltons, because it has been found that the improved soluble β-glucan falls between those molecular weight ranges.

An additional measure of product-related impurities is reducing sugar. Each glucan polysaccharide chain ends in the aldehyde form (reducing sugar) of the sugar. Thus, the amount of reducing sugar serves as an indication of the number of chains in the preparation. Because a new reducing end is generated with each chain cleavage, reducing sugar is a monitor of chain stability. Reducing sugars can be measured by the bicinchoninic acid (BCA) assay, which is well known in the art.

Potential process impurities include other yeast cell constituents such as DNA, yeast cell proteins, lipids and other polysaccharides such as glycogen, mannan and chitin. DNA levels can be analyzed using the slot hybridization assay (MDS PanLabs, Seattle, Wash.). Residual protein may be determined by a colorimetric assay for protein or by a more sensitive commercial enzyme-linked immunosorbent assay (ELISA) that measures *S. cerevisiae* cell proteins (Cygnus Technology, Southport, N.C.). Residual lipids may be monitored by evaluating ergosterol levels using reversed-phase high-performance liquid chromatography (Rβ-HPLC) with detection at 280 nm.

Glycogen is a polysaccharide comprised primarily of α-1,4-linked glucose, and its presence can be determined by an enzymatic assay. The product is added to an enzymatic reaction containing amyloglucosidase, which liberates glucose from glycogen, generating reducing sugars. The reducing sugars are measured by the BCA assay.

Mannan is a branched polymer of α-1,6-linked mannose with α-1,2- and α-1,3-branches that is monitored, as mannose, by its monosaccharide composition. The product is added to a reaction, and the mannose is hydrolyzed with trifluoroacetic acid and analyzed by HPLC.

Chitin is a polymer of β-1,4-N-acetyl glucosamine, which is monitored by a calorimetric assay. Soluble β-glucan is hydrolyzed with sulphuric acid, and the resulting glucosamine forms a complex with Ehrlich's reagent that is measured calorimetrically. These and other suitable assays are known to those skilled in the art.

Potential non-yeast impurities originating from components added during the manufacturing process include Triton X-100 (surfactant) and Antifoam 204 (antifoaming agent). Reversed-phase HPLC (Rβ-HPLC) with detection at 280 nm can be used to discern any residual Triton X-100. Antifoam 204 is assessed by a Rβ-HPLC method using selective ion monitoring with an electrospray mass spectroscopy detector in positive mode.

Certain product specifications are proposed for utilizing the soluble β-glucan as a pharmaceutical agent. These specifications are listed in Table 3.

TABLE 3

| Category | Attribute | Method | Proposed Limits |
|---|---|---|---|
| General | Appearance | Visual | Clear, colorless solution |
|  | pH | pH meter | 5.0-7.5 |
|  | Osmolality | osmometer | 260-312 mOsm |
| Identity | HR-GPC profile | GPC-MALS | Conforms to standard; ratio of peak retention volumes: 0.8-1.2 |
| Strength | Concentration (total hexose) | Colorimetric hexose assay | 0.85-1.15 mg/ml |
| Impurities | HMW material | GPC-MALS | ≤10% |
|  | LMW material | GPC-MALS | ≤17% |
|  | Reducing sugar | BCA assay | 0.7-1.6% of total hexose |
|  | Residual protein | Colorimetric protein assay | ≤0.2% of total hexose |
|  | Chitin (glucosamine) | Colorimetric assay | ≤2% of total hexose |
|  | Mannan (mannose) | Monosaccharide composition | ≤1% of recovered hexose |
|  | Glycogen | Enzymatic | ≤10% of total hexose |
| Safety | Endotoxin | PyroGene recombinant Factor C assay | ≤0.25 EU*/ml |
|  | Bioburden | Membrane filtration | ≤5 CFU**/10 ml |

*colony forming unit
**endotoxin unit

As stated above, soluble β-glucan produced by methods 10 and 24 is an improved product over prior art soluble β-glucan materials. Improvement is seen in clinical trial results where soluble β-glucan of the present invention given at a much higher maximum dose showed the same or fewer adverse events (AEs) as lower maximum doses of prior art soluble β-glucan. The results are shown in Table 4.

TABLE 4

| Related AE (occurring in ≥5% of total participants) | Bf1[1] | Improved Soluble β-Glucan[2] |
|---|---|---|
| Body as a whole | | |
| Back pain | 7% | — |
| Fever | 16% | — |
| Headache | 30% | 8% |
| Pain | 7% | — |
| Cardiovascular | | |
| Vasodilation/Flushing | — | 6% |
| Digestive | | |
| Nausea | 7% | 6% |
| Hemic/lymphatic | | |
| Ecchymosis | — | — |
| Leukocytosis | — | — |
| Respiratory | | |
| Dyspnea | — | 1% |
| Musculoskeletal | | |
| Athralgia | 11% | — |
| Skin/appendages | | |
| Urticaria | 7% | — |
| Rash | — | — |
| Special senses | | |
| Conjunctivitis | 9% | — |

[1]maximum single dose 2.25 mg/kg
[2]maximum single dose 6.0 mg/kg

Bf1 is known by the tradename Betafectin™, a soluble β-glucan product developed by Alpha-Beta Technology, Inc. The process to produce Betafectin™ utilized formic acid to solubilize particulate β-glucan material. In addition, Bf1 was not subjected to any chromatography in its purification process.

The studies were performed with a volunteer population of healthy subjects. When compared to Bf1, study participants taking the improved soluble β-glucan reported fewer adverse events even though the maximum dosage was more than 2.5 times that of Bf1. Thus, a much higher dosage of the improved soluble β-glucan can be given at least without increasing, but likely actually even decreasing, side effects. In addition, the improved soluble β-glucan does not induce biochemical mediators, such as interleukin-1β and tumor necrosis factor-α, which cause inflammatory side effects.

The processes of the present invention provide several advantages over prior art processes and result in improved β-glucan products. The particulate β-glucan is essentially free of harmful VOCs. Solubilization of β-glucan is safer and more economical. In addition, solubilization of particulate β-glucan made by the present process results in soluble β-glucan with improved pharmaceutical qualities.

While this invention has been shown and described with references to particular embodiments, it will be understood by those skilled in the art that various changes in form and detail may be made therein without departing from the spirit and scope of the invention encompassed by the appended claims.

The invention claimed is:

1. A process for producing underivatized, soluble β-glucan derived from *Saccharomyces cerevisiae* and having immunostimulating properties and an average molecular weight between about 120,000 Da and about 205,000 Da; soluble β-glucan having a molecular weight over 380,000 Da in an amount less than or equal to 10%; and β-glucan having a molecular weight under 25,000 Da in an amount less than or equal to 17%, the process comprising:

applying pressure to a suspension comprising particulate β-glucan and acetic acid; and heating the suspension for a time sufficient to form the soluble β-glucan, wherein the suspension is buffered to a pH of about 3.6, and wherein the underivatized, soluble β-glucan is not treated with caustic solution during the process.

2. The process of claim 1 and further comprising: clarifying the soluble β-glucan.

3. The process of claim 2 wherein the soluble β-glucan is clarified by centrifugation, filtration or a combination thereof.

4. The process of claim 1 wherein the suspension is in a vessel in which substantially all oxygen is removed.

5. The process of claim 4 wherein the oxygen is removed by purging the vessel with nitrogen.

6. The process of claim 1 and further comprising: separating the soluble β-glucan into fractions based on molecular weight.

7. The process of claim 6 wherein the soluble β-glucan is separated by chromatography.

8. A composition comprising:
underivatized, soluble β-glucan derived from *Saccharomyces cerevisiae* and having immunostimulatory properties and an average molecular weight between about 120,000 Da and about 205,000 Da;
soluble β-glucan having a molecular weight over 380,000 Da in an amount less than or equal to 10%; and β-glucan having a molecular weight under 25,000 Da in an amount less than or equal to 17%,
wherein the underivatized, soluble β-glucan is prepared by applying pressure to a suspension comprising particulate β-glucan and acetic acid, and heating the suspension for a time sufficient to form the soluble β-glucan, wherein the suspension is buffered to a pH of about 3.6, and wherein the underivatized, soluble β-glucan is not treated with caustic solution during preparation.

9. The composition of claim 8 where the underivatized, soluble β-glucan forms a triple helix aggregate having a molecular weight between about 25,000 Da and about 380,000 Da.

10. The composition of claim 8 where the underivatized, soluble β-glucan is prepared by applying about 35 PSI of pressure to the suspension.

11. The composition of claim 8 where the underivatized, soluble β-glucan is prepared by heating the suspension to about 135° C.

12. The composition of claim 8 where the underivatized, soluble β-glucan has a molecular weight over 380,000 Da in an amount of from 4% to 8%.

13. The composition of claim 8 where the underivatized, soluble β-glucan has a molecular weight under 25,000 Da in an amount of from 8% to 13%.

14. The composition of claim 8 where the underivatized, soluble β-glucan has a reducing sugar of from 1.0% to 1.1% of total hexose.

15. The composition of claim 8 where the suspension is heated in the presence of about 0.61 g of sodium acetate and about 5.24 ml glacial acetic acid per liter of the suspension.

16. The composition of claim 8 where the underivatized, soluble β-glucan is prepared in the presence of nitrogen.

17. The composition of claim 8 where the preparation of the underivatized, soluble β-glucan does not use formic acid or sulfuric acid.

18. The composition of claim 8 where the soluble β-glucan is purified by chromatography.

19. The composition of claim 8 where the soluble β-glucan is purified by hydrophobic interaction chromatography.

* * * * *